(12) United States Patent
Stasi et al.

(10) Patent No.: US 6,344,274 B1
(45) Date of Patent: *Feb. 5, 2002

(54) LOW THICKNESS ANTIFRAGMENTATION PLATES

(75) Inventors: Alberto Luca Stasi, Rho; Donato Stanco, Barbaiana, both of (IT)

(73) Assignee: Atofina, Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/917,109

(22) Filed: Aug. 25, 1997

(30) Foreign Application Priority Data

Aug. 28, 1996 (IT) .......................................... MI96A1796

(51) Int. Cl.$^7$ ........................... B32B 27/30; B32B 27/40
(52) U.S. Cl. ..................... 428/424.2; 428/213; 428/520
(58) Field of Search ............................... 428/411.1, 480, 428/500, 515, 520, 522, 423.1, 424.2, 911, 220, 332, 213; 522/90, 92, 96, 103

(56) References Cited

U.S. PATENT DOCUMENTS

| | | | | |
|---|---|---|---|---|
| 3,653,950 A | * | 4/1972 | Bonsignore | 117/72 |
| 4,322,476 A | * | 3/1982 | Molaris, Jr. | 428/412 |
| 4,355,077 A | * | 10/1982 | Chevreux et al. | 428/412 |
| 4,445,953 A | | 5/1984 | Hawk | 156/102 |
| 4,594,290 A | * | 6/1986 | Fischer et al. | 425/212 |
| 4,829,123 A | * | 5/1989 | Shigematsu et al. | 525/28 |
| 4,929,506 A | * | 5/1990 | Kerr, III et al. | 428/412 |
| 5,040,352 A | * | 8/1991 | Oberlander et al. | 52/789 |
| 5,318,737 A | * | 6/1994 | Trabert et al. | 264/171 |
| 5,438,106 A | * | 8/1995 | Siranovich et al. | 525/440 |
| 5,506,051 A | * | 4/1996 | Levy-Borochov et al. | 428/332 |

FOREIGN PATENT DOCUMENTS

| | | |
|---|---|---|
| EP | 0 771 912 A1 | 5/1997 |
| EP | 0771912 A  * | 5/1997 |

* cited by examiner

Primary Examiner—Paul Thibodeau
Assistant Examiner—D. Lawrence Tarazano
(74) Attorney, Agent, or Firm—Arent, Fox, Kintner, Plotkin & Kahn

(57) ABSTRACT

Multilayer transparent, antireflex, coloured or opaline plates, with smooth or embossed surfaces, optionally thermouldable with external layers in acrylic polymers, low thickness, in the range of 1.5 up to lower thicknesses of 10 mm, by employing one or more polymeric continuous films which have the property to have elastic modulus lower than the one of PMMA of at least 30%, and/or elongation at break higher than at least 40%, measured by the test according to ISO 527 for plates or films, placed inside the panel.

10 Claims, No Drawings

LOW THICKNESS ANTIFRAGMENTATION PLATES

The present invention relates to multilayer transparent, antireflex, coloured or opaline, laminates having smooth or embossed surfaces, optionally thermomouldable with external layers of acrylic polymers, obtained by coextrusion or by compression molding or by casting, the laminates have anti-fragmentation properties and/or improved mechanical properties for use in building or in signs, in lighting, and in the medical field, etc.

In particular the invention relates to polymethylmethacrylate laminates with low thickness, in the range of 1.5 up to lower less than of 10 mm in thickness, preferably 2–5 mm.

The technical problem arises when a blunt instrument crashes into the panel or into the manufactured article obtained from the laminate the impact results in the formation of several fragments which cause undesired situations or of danger for whom and/or what lies under these structures.

Therefore an object of the present invention relates to panels/manufactured articles exhibiting superior antifragmentation properties and/or improved mechanical properties with respect to the crash.

The Applicant has unexpectedly and surprisingly found that it is possible to produce antifragmentation laminates based on acrylic polymers employing one or more polymeric continuous films which have an elastic modulus lower than that by PMMA of at least 30%, and/or elongation at break higher than at least 40, preferably of at least 60G measured by the test according to ISO 527 for laminates or films, or similar standards, placed inside the panel.

If only one film is utilized it can be placed about approximately in the middle of the panel, preferably it is placed closer to the tensile stress part during the impact (opposite surface to the surface subject to crash). In practice the film is placed preferably at a distance between 10 and 40% of the total thickness of the laminate with respect to the surface opposite to the surface subject to impact. It is also possible to produce the plate with two film insertions placed near both PMMA faces. According to a preferred embodiment of the invention additional films can also be inserted in the tensile stress part at distances generally of about 1 mm from each other.

The film has a thickness generally from 70 $\mu$m up to 3 mm, preferably from 90 $\mu$m to 2 mm. In the case of the preferred panels of the invention (2–5 mm), the film has a thickness comprised from 70 $\mu$m to about 1.5 mm, preferably from 100 $\mu$m to 1 mm.

The preferred polymers are transparent polyalkylenterephthalates with the alkyl of from 2 to 5 carbon atoms, for instance polyethylenterephthalate (PET), polybutylenterephthalate (PBT); polyvinylbutyral (PVB), transparent elastomers having an acrylic basis, transparent thermoplastic elastomers having a styrenic basis such as styrene/butadiene block copolymers, MBS type transparent copolymers having a styrenic basis, grafted polymers having a vinylic basis, such as maleic anhydride.

Polymeric films carried out by polymerization with ultraviolet light which comprise the following essential components:

(a) selected from the following components:
(a1) alkyl(meth)acrylate monomers having general formula:

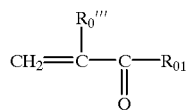

wherein
$R_0'''$ can be H, $CH_3$
$R_{01}$ can be an alkyl from 1 to 10 carbon atoms, linear or branched when possible, preferably a linear alkylic chain, preferably from 1 to 6 carbon atoms, or a cycloalkyl alkyl from 5 to 15 carbon atoms, optionally containing heteroatoms, for instance cyclopenthyl or cyclohexyl;

(a2) aliphatic urethane oligomers di (tri) (meth) acrylates obtainable by reaction of a polyisocyanate, preferably di-tri-isocyanate having the general formula:

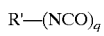

wherein R' is an aliphatic chain from 1 to 10 carbon atoms, preferably from 2 to 6, or an (alkyl) cycloaliphatic chain wherein the alkyl has the meaning described above and the cycloalkyl is a cyclic ring from 3 to 6 carbon atoms, preferably 5–6,
q being an integer from 2 to 6, preferably from 2 to 3, with
dialcohols of general formula:

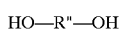

wherein R" has the same meaning as R'; said prepolymer NCO or OH terminated is reacted with (meth)acrylic acid to obtain unsaturated terminations;

(a1) and (a2) can be also in admixture with each other, the amount of (a2) ranging from 20 to 80% by weight with respect to (a1), preferably between 20–40% by weight;

(b) selected from one or more of the following components:

(b1) polyalkylglycols di-poly-(meth)acrylates having the general formula:

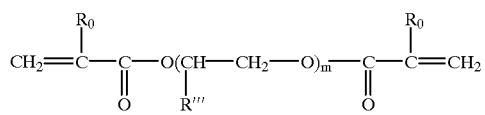

wherein
$R_0$ is equal to H, $CH_3$
R''' is equal to H, alkyl from 1 to 6 carbon atoms, preferably 1,
m is an integer from 2 to 12, preferably from 3 to 10;

(b2) alkyl di-poly-(meth)acrylates having the general formula:

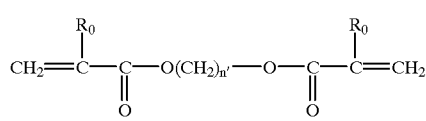

wherein
$R_0$ is equal to H, $CH_3$,
n' is an integer from 2 to 10, preferably from 4 to 6;

(b3) polyallylglycidylethers having the general formula:

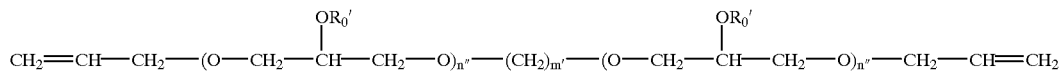
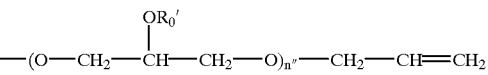

wherein
n" is an integer from 1 to 8, preferably from 3 to 6,
m' is an integer from 2 to 10, preferably from 2 to 6,
$R_{0'}$ is equal to H or an alkyl from 1 to 10 carbon atoms, preferably from 1 to 6;
the mixture of (a) and (b) is such as to have a viscosity from 50 to 3,000 cPoises, preferably from 100 to 1,000;
the component (b) can be omitted if in the formulation the component (a2) is present;

(c) hydroxy or carboxy alkyls alkyl(meth)acrylate from 2 to 6 carbon atoms, in amounts comprised between 0.5 and 5% by weight on the total, preferably 0.5–2, having the general formula:

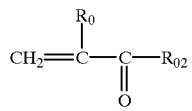

wherein
$R_0$ is H or $CH_3$,
$R_{02}$ is an alkyl from 1 to 10 carbon atoms, preferably from 1 to 6;
the amount of component (b) in the composition being comprised between 5 and 20% by weight, preferably between 5 and 10% by weight;
the film being obtained by UV polymerization in the presence of photoinitiators in amounts comprised between 1 and 10% by weight, preferably between 3 and 6% by weight;
the amount of (a) being the complement to 100.

The components of type (a2) are commercially known for instance as EB®: such as EB 230, EB 264, EB 284, EB 244 produced by the company UCB.

The components of type (a1) are for instance methyl-, ethyl-, butyl-, isobutyl-, ethyl-hexyl acrylate, etc.

The compounds (b1) are also known commercially as: SARTOMER® 252, SARTOMER® 400, commercialized by Cray Valley, or tripropylenglycoldiacrylate (TPGDA); compounds (b2) are well known, hexandioldiacrylate (HDDA) can be mentioned; compounds (b3) are known in trade as SANTOLINK® XI 100 commercialized by Monsanto.

Compounds (c) which can be mentioned are hydroxyethyl- and hydroxypropyl-acrylates o-methacrylates; alpha-hydroxyethyl(meth)acrylate, carboxyethyl(meth)acrylate, for instance 2-carboxyethyl (meth)acrylate, are preferred.

These polymers can be used alone or in admixture with each other or with other polymers, for instance PMMA, MMA/-styrene in such ratios as to maintain the transparence and the elongation and modulus properties as defined above.

As polymerization photoinitiators of radical type, induced by ultraviolet light, one can those based on benzophenone such as ESACURE® KT 37 and UVECRYL® P115 by Lamberti, or such as IRGACURE® 500 by Ciba-Geigy. DAROCUR® 1173 and the other compounds disclosed in EP patent 374,516 can also be utilized; alkylic or aromatic peroxides and/or hydroperoxides, for instance benzene peroxide, ter-butylhydroperoxide, laurylperoxide, lauroylperoxide, cumylhydroperoxide, etc. can also be utilized. The amount of radicalic photoinitiators as said above ranges from 0.5 to 5% by weight, preferably from 0.5 to 2% by weight.

Panels having an acrylic basis containing antifragmentation polymers can be obtained by compression moulding, by casting, by coextrusion or by sizing.

The industrially preferred process for preparing the antifragmentation panels of the present invention is coextrusion utilizing a feed-block or optionally a head having separated channels. The usual procedures to eliminate and/or reduce the possible encapsulation and unstability phenomena at the interface among the various polymer layers are obviously to be carried out. Generally the thermal profiles of the extruders utilized for the various materials are such as to reduce the viscosity differences of the various polymeric melts, in the limits of the process conditions of the single materials. It is preferable degas to and dry the polymers before their use i.e. prior to an extrusion. In particular, in the case of the examples reported hereunder, the materials utilized have been dried with a stove under vacuum: for instance at 80° C. for at least 16 hours for acrylic polymers and 60° C. for 12 hours for styrene butadiene block copolymers. The utilized device for calendering is preferably a three cylinders device with independent motors.

Another process for producing the panels in question is by casting films polymerizable by UV described hereinunder.

Two PMMA (cast or extruded) laminates are taken and, are then superimposed and fixed to each other by overlapping at the borders of the laminates a biadhesive tape, for instance the product commercialized by 3M as VHB®, having a thickness of some millimeters, in order to form an interspace of the same sizes of the laminates and thickness of the tape, taking care however of leaving one or more openings depending on the laminates size. This allows for the filling of the interspace with the UV polymerizable resin of the invention. The amount of resin is determined by considering besides the volume of the interspace also the dimensional shrinkage of the composition of the invention during the polymerization phase. The so obtained panel is inserted inside an oven equipped with UVA lamps and kept therein for the time necessary to achieved polymerization. Since this kind of lamps does not give rise to a strong increase of the temperature of the panel under preparation, the possible stresses of the panel, which could compromise the properties thereof, are thus avoided.

Crosslinking besides with the radicalic photoinitiators indicated above, can be also accomplished using mixed type radicalic and cationic photoinitiators. Polymerization and crosslinking cationic initiators with UV light are well known in the art, for instance triarylsulphonium salts, such as hexafluoroantimonates of triarylsulphonium (UVI-6974-CYRACURE®, Union Carbide) and hexafluorophosphates of triarylsulphonium (UVI-6990-CYRACU-RE®, Union Carbide), can be mentioned.

Such cationic photoinitiators are not inhibited by the oxygen and are employed in combination with radicalic photoinitiators preferably in a weight ratio between radicalic/cationic photoinitiator of at least 2/1, more preferably of 3/1. By employing such ratios it is possible to obtain the resin crosslinking in an air room with relative humidity of up to 60.

The cationic photoinitiator amount generally ranges from 0.01 to 3% by weight, preferably from 0.2 to 0.6.

Crosslinking with radicalic photoinitiators is generally carried out for times comprised between 30 sec-30 min depending on the lamp power, on the distance between panel and lamp, generally depending on the radiant power really reaching the panel to be polymerized.

The panels with the film according to the present invention can be resistant to an impact energy according to the test indicated in the examples.

Impact resistance is determined if the panel breaks without producing fragments, that is if fragments are retained by the film, or one merely determines the number of fragments of the panel. In the latter case, the panels of the invention when subjected to breaking forces give rise to an extremely limited number of fragments, generally of a few units, in practice they break into two fragments.

As elastomers having an acrylic basis, both homopolymers, for instance polybutyl(meth)acrylate and copolymers having also complex core-shell type structures, having one or more layers, similar to those generally used for impact-resistant PMMA, can be utilized.

As an example of elastomeric products having an acrylic basis see U.S. Pat. No. 5,183,851, U.S. Pat. No. 3,793,402, U.S. Pat. No. 3,808,180 and 4,180,529 incorporated herein by reference.

The films of the polymers utilized according to the present invention show a good adhesion with the acrylic polymers of the panels.

In case of poor adhesion it can be improved by using suitable bonding agents, transparent if the final composite must be transparent. For instance in case of PET and PBT, the bonding agents commercialized by the film suppliers are used. One can generally use bonding agents having an acrylic, butadiene, chloroprene, nitrilic, butyl, etc. basis, obviously selected on the basis of the chemical nature of the intermediate film.

For the elastomers having an acrylic or styrenic basis, the compatibility with PMMA is generally sufficient as such to assure a good adhesion.

For the films carried out via UV the product assuring the adhesion is already incorporated in the mixture to be polymerized (product C).

The polymers to obtain the films of the invention are well known in the art and in trade.

The preferred polymers are the polymers curable via UV as indicated above, the block styrene/butadiene copolymers. These latter are in trade as K RESIN by Phillips Petroleum.

Among the styrenic polymers, MBS terpolymer methylme-thacrylate-butadiene-styrene can also be mentioned.

With the preferred polymers uniform film with good adhesion to the acrylic basis is obtained, with the K resin bonding agents are not needed, for the reasons indicated above.

The panels with the film according to the present invention can be resistant to an impact energy according to the test described in the examples of multilayer plates obtained by the coextrusion technology indicated above.

Moreover accelerated ageing tests with QUVB lamps have shown that the inner layer of the film does not suffer ageing relative to the optical and mechanical properties even after 1000 hours of exposure or more. This is an advantage of the panels of the present invention since it is well known that films, for instance based on K-Resin as such, quickly age when exposed outside. This generally allows one to utilize films of the invention without requiring the use of a particular addition to increase the resistance to ageing. This brings process simplifications and leads also to a reduction in production costs.

Polymers having an acrylic basis according to the present invention are MMA homopolymers, MMA copolymers with other comonomers such as ethyl(meth)acrylate, butyl-(meth)acrylate in low concentrations. The amounts of comonomer are generally up to 10% by weight. MMA homopolymers or copolymers can be obtained by polymerization according to usual techniques, for instance by polymerization in mass or in suspension. The molecular weight can be adjusted by the addition of suitable chain transfer agents, for instance of the mercaptanes class. The weight average molecular weights $M_w$ can generally be comprised in the range of 50,000–2,000,000.

The lowest values of molecular weight are preferred for the production of laminates by co(extrusion); the highest ones in case of preparation of laminates by casting.

One can also be used commercial impact-resistant PMMA, as an acrylic based polymer for the preparation of the external layers. Generally the impact-resistant PMMA contains an MMA homopolymer or copolymer as indicated above and in general from 20–50% by weight of an acrylic based elastomer, preferably having core-shell structures as indicated above for the films.

As examples of elastomeric products with an acrylic basis see for instance U.S. Pat. Nos. 5,183,851, U.S. Pat. No. 3,793,402, U.S. Pat. Nos. 3,808,180 and 4,180,529, herein incorporated for reference.

The following examples are given only for illustrative purposes and are not deemed to limit of the present invention.

EXAMPLE 1

A three layer transparent coextruded laminate with smooth surfaces was prepared; for the different layers the following materials were utilized:
  Layer 1: thickness 1.9 mm obtained from colourless 3000 Altuglas$^{(R)}$ GR9E by ATOHAAS,
  Layer 2: thickness 1.0 mm obtained from K-Resin$^{(R)}$ 05 by Phillips Petroleum
  Layer 3: thickness 1.1 mm obtained from colourless Altuglas$^{(R)}$ GR9E of the same type as layer 1.

Antifragmentation Tests

A laminate sample as described above having dimensions of 118 mm×118 mm was placed on a square support having sides of 120 mm with a support frame of 5 mm is struck in the middle on the part of layer 1 by a steel sphere having a diameter of 54 mm and a weight of 0.63 kg by letting it fall from an height of 86 cm. After the crash the plate appears broken but the fragments generated are kept perfectly together.

The same antifragmentation test reported above repeated on a sample of a 4 mm PMMA plate as such, brings to the formation of several fragments which disperse after the impact.

EXAMPLE 2

A white opaline three layer coextruded plate with smooth surfaces was prepared; for the different layers the following materials were utilized:
  Layer 1: thickness 1.9 mm obtained from white 008 Altuglas$^{(R)}$ GR9E by ATOHAAS, Layer 2: thickness 1.0 mm obtained from K-Resin$^{(R)}$ 05 by Phillips Petroleum Layer 3: thickness 1.1 mm obtained from white 008 Altuglas$^{(R)}$ GR9E by ATOHAAS.

Antifragmentation Tests

A laminate sample as described above having dimensions of 118 mm×118 mm was placed on a square support having sides of 120 mm with support frame of 5 mm. The laminates is struck in the middle on the part of layer 1 by a steel sphere having a diameter of 54 mm and a weight of 0.63 kg, by letting it fall from an height of 86 cm. After the crash the laminate appears broken but the fragments produced are kept perfectly together.

EXAMPLE 3

An antireflex three layer transparent coextruded laminate with a matt surface was prepared. The antireflex effect was obtained by utilizing the second cylinder of the satinized calender; for the different layers the following materials were utilized:

Layer 1: thickness 1.9 mm obtained from colourless 3000 Altuglas$^{(R)}$ GR9E by ATOHAAS, Layer 2: thickness 1.0 mm obtained from K-Resin$^{(R)}$ 05 by Phillips Petroleum Layer 3: thickness 1.1 mm obtained from colourless 3000 Altuglas$^{(R)}$ GR9E by ATOHAAS.

Antifragmentation Tests

Example 2 was repeated with the coextruded plate indicated above and the test piece was struck in the middle on the part of layer 1 (smooth surface) by a steel sphere equal to that of example 2. After the crash the laminate appears broken but the fragments produced are kept perfectly together.

EXAMPLE 4

A four layer coextruded transparent laminate with an antireflex surface was prepared; for the different layers the following materials were utilized:

Layer 1: thickness 2 mm obtained from colourless 3000 Altuglas$^{(R)}$ GR9E by ATOHAAS, Layer 2: thickness 1.0 mm obtained from K-Resin$^{(R)}$ 05 by Phillips Petroleum Layer 3: thickness 0.5 mm obtained from colourless 3000 Altuglas$^{(R)}$ GR9E by ATOHAAS.

Layer 4: (for obtaining the antireflex surface): thickness 1.0 obtained from Altuglas$^{(R)}$ GR9E XD.

Antifragmentation Tests

The same test reported in Example 2 was repeated. After the crash the laminate appears broken but the fragments produced are kept perfectly together.

The same test repeated on a 4.5 mm PMMA laminate as such several fragments were produced which dispersed after the impact.

EXAMPLE 5

Example 1 was repeated but by carrying out the antifragmentation test, letting fall the steel sphere from an height of 210 cm. In such case the test piece broke but produced only two fragments in turn formed by various fragments kept at any rate perfectly together by the layer of the intermediate film.

EXAMPLE 6

Example 2 was repeated but by utilizing in layer 2 K-Resin$^{(R)}$ KK38 by Phillips Petroleum instead of K-Resin$^{(R)}$ 05. The antifragmentation results are similar to those of Ex. 2.

What is claimed is:

1. An antifragmentation, transparent, antireflex, colored or opaline multi-layer laminate with smooth or embossed surfaces, having a thickness from 1.5 to less than 10 mm and external layers of polymethyl methacrylate (PMMA) polymers, and including one or more polymeric continuous films between said external layers, said films obtained by polymerization of a composition with ultraviolet light, wherein said composition comprises the following components:

(a) selected from the group consisting of:

(a1) alkyl(meth)acrylate monomers having the formula:

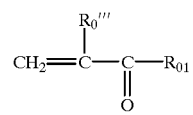

wherein $R_0'''$ is H or $CH_3$, and $R_{01}$ is an alkyl from 1 to 10 carbon atoms, linear or branched, a linear alkylic chain, or a cycloalkyl alkyl from 5 to 15 carbon atoms, optionally containing heteroatoms;

(a2) aliphatic urethane oligomers di(tri)(meth)acrylates obtainable by reaction of a polyisocyanate, having the formula:

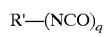

wherein R' is an aliphatic chain from 1 to 10 carbon atoms, or an (alkyl)cycloaliphatic chain wherein the alkyl has the meaning described above and the cycloalkyl is a cyclic ring from 3 to 6 carbon atoms, and q is an integer from 2 to 6, with dialcohols having the formula:

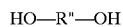

wherein R" has the same meaning as R';

said prepolymer NCO or OH terminated are reacted with (meth)acrylic acid to obtain unsaturated terminations;

or an admixture of (a1) and (a2), the amount of (a2) ranging from 20 to 80 percent by weight with respect to (a1);

(b) at least one member selected from the group consisting of:

(b1) polyalkylglycols di-poly-(meth)acrylates having the formula:

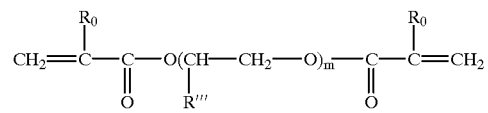

wherein $R_0$ is H or $CH_3$,

R'" is H or alkyl from 1 to 6 carbon atoms, and m is an integer from 2 to 12, (b2) alkyl di-poly-(meth)acrylates having the formula:

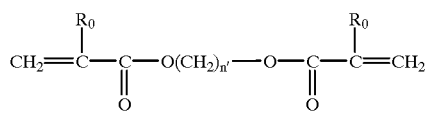

wherein
$R_0$ is H or $CH_3$, and
n' is an integer from 2 to 10;

(b3) polyallylglycidylethers having the formula:

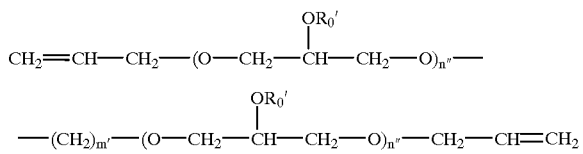

wherein
n" is an integer from 1 to 8,
m' is an integer from 2 to 10, and
$R_0'$ is H or an alkyl from 1 to 10 carbon atoms,
wherein if (a2) is present, (b) is optionally present,
wherein the amount of (b), if present, is between 5 and 20% by weight based on the total weight of the composition, and the mixture of (a) and (b), if present, has a viscosity from 50 to 3,000 cPoises;

(c) hydroxy or carboxy alkyls alkyl(meth)acrylate from 2 to 6 carbon atoms, in amounts of between 0.5 and 5% by weight based on the total weight of the composition, and having the formula:

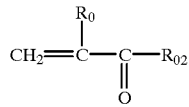

wherein
$R_0$ is H or $CH_3$, and
$R_{02}$ is an alkyl from 1 to 10 carbon atoms; and (d) polymerization photoinitiators, in amounts of between 1 and 10% by weight based on the total weight of the composition;
the amount of (a) being the remainder to 100% of the total weight of the composition.

2. Multilayer laminate according to claim 1, wherein one or more continuous polymeric films form the center layers of the laminate.

3. Multilayer laminate according to claim 1, wherein the film is placed at a distance comprised between 10 and 40% of the total thickness of the laminate with respect to the surface opposite to the surface subject to impact, and optionally a second film is placed near the surface subject to the [crash] impact at the same distances indicated above.

4. Multilayer laminate according to claim 1, wherein a plurality of films are spaced at distances generally of about 1 mm from each other.

5. Multilayer laminate according to claim 1 wherein the film has a thickness between 100 $\mu$m and 1 mm when the thickness of the laminate is 2–5 mm.

6. Multilayer laminate according to claim 1, wherein the polymerization photoinitiators are radicalic photoinitiators which are induced by ultraviolet light, optionally in the presence of cationic photoinitiators, wherein if the cationic photoinitiators are present, the ratio between the radicalic/cationic photoinitiators is at least 2/1.

7. Multilayer laminate according to claim 1, wherein the external layers are obtained by casting, by compression molding, by coextrusion or by sizing.

8. Multilayer laminate according to claim 7, obtained by coextrusion.

9. Multilayer laminate according to claim 7, obtained by casting.

10. Multilayer laminate according to claim 7, wherein bonding agents are utilized for adhering the film to the PMMA polymers.

* * * * *